(12) United States Patent
Brumbach et al.

(10) Patent No.: US 7,158,890 B2
(45) Date of Patent: Jan. 2, 2007

(54) SYSTEM AND METHOD FOR PROCESSING INFORMATION RELATED TO LABORATORY TESTS AND RESULTS

(75) Inventors: David Brumbach, Denver, PA (US); Lynne Malchiodi, King of Prussia, PA (US); Jeffery Hunsberger, Limerick, PA (US); Susan Brunstetter, Downingtown, PA (US)

(73) Assignee: Siemens Medical Solutions Health Services Corporation, Malvern, PA (US)

( * ) Notice: Subject to any disclaimer, the term of this patent is extended or adjusted under 35 U.S.C. 154(b) by 4 days.

(21) Appl. No.: 10/802,712

(22) Filed: Mar. 17, 2004

(65) Prior Publication Data

US 2004/0204910 A1    Oct. 14, 2004

Related U.S. Application Data

(60) Provisional application No. 60/455,934, filed on Mar. 19, 2003.

(51) Int. Cl.
*G06F 19/00* (2006.01)
(52) U.S. Cl. ............................................. 702/19; 435/4
(58) Field of Classification Search ................... 702/19, 702/22–23, 26, 31–32, 81–82, 84, 182–183; 700/28, 32, 37, 79–80, 83, 108–109, 266; 600/300; 435/5
See application file for complete search history.

(56) References Cited

U.S. PATENT DOCUMENTS

| | | | | |
|---|---|---|---|---|
| 5,369,566 A | * | 11/1994 | Pfost et al. | 700/18 |
| 5,789,173 A | * | 8/1998 | Peck et al. | 435/6 |
| 5,888,756 A | * | 3/1999 | Ralston | 435/14 |
| 5,937,364 A | * | 8/1999 | Westgard et al. | 702/83 |
| 6,317,639 B1 | * | 11/2001 | Hansen | 700/83 |
| 6,450,956 B1 | * | 9/2002 | Rappaport et al. | 600/300 |
| 6,500,117 B1 | | 12/2002 | Hancock, Jr. | 600/300 |
| 6,725,180 B1 | * | 4/2004 | Mayer et al. | 702/188 |
| 6,753,186 B1 | * | 6/2004 | Moskoff | 436/125 |
| 6,830,731 B1 | * | 12/2004 | Buechler et al. | 422/82.08 |
| 7,124,031 B1 | * | 10/2006 | Hoffman et al. | 702/19 |
| 2002/0107641 A1 | * | 8/2002 | Schaeffer et al. | 702/19 |
| 2002/0155541 A1 | * | 10/2002 | Naughton et al. | 435/69.1 |
| 2003/0014222 A1 | | 1/2003 | Klass et al. | 702/190 |
| 2003/0158468 A1 | | 8/2003 | Iliff | 600/300 |

* cited by examiner

*Primary Examiner*—Marc S. Hoff
*Assistant Examiner*—Mary Catherine Baran
(74) *Attorney, Agent, or Firm*—Alexander J. Burke

(57) ABSTRACT

A system and method are provided that addresses the need for an improved microbiology validation system that monitors and validates clinical culture laboratory test results as they occur throughout the testing lifecycle of a clinical culture. Techniques are provided that consider the results of earlier performed tests when entering results for later performed tests so that inconsistent or wrong test results of a patient are not inadvertently released to a physician for review.

25 Claims, 14 Drawing Sheets

| 30 | 32 | 34 |
|---|---|---|
| FIELD IN THE UDT FORM | DESCRIPTION | CORRESPONDING dB COLUMN |
| TEST (208) | DISPLAYS THE TEST THAT IS BEING VALIDATED | Test.test_id |
| PERF INSTITUTION (210) | SELECT THE PERFORMING INSTITUTION WHERE THIS VALIDATION WILL BE EVALUATED. | HOSP |
| VALIDATION SEVERITY (226) | SELECT INFO, WARN, OR FAIL | Svre_mne |
| OVERRIDE CMNT REQ? (228) | SELECT THIS WHEN A REASON FOR OVERRIDE COMMENT IS REQUIRED | Ovrd_cmnt_req_ind |
| RESULT (212) | SELECT * (ANY), IN, NI, OR = ENTER THE RESULT THAT WILL INDICATE WHEN THE VALIDATION WILL BE EVALUATED | Vld_test_qlfy AND rslt_text_val |
| ORG GRP PRIO (214) | VALUE ENTERED BASED ON THE PRIORITY DEFINED IN THE ORGANISM GROUP UDT. | Org_grp_prio_no |
| CULTURE TEST (218) | ENTER THE CULTURE TEST(S) THAT WILL BE TAKEN INTO CONSIDERATION WHEN DETERMINING IF THIS VALIDATION SHOULD BE EVALUATED. | Cult_test_qlfy AND cult_test_parm_val |
| SOURCE (220) | ENTER THE SOURCE(S) THAT WILL BE TAKEN INTO CONSIDERATION WHEN DETERMINING IF THIS VALIDATION SHOULD BE EVALUATED. | Src_qlfy AND src_parm_val |
| VALIDATION DESCRIPTION (222) | ENTER A DESCRIPTION (250 CHARACTER MAX), THAT SPECIFICALLY DESCRIBES THIS VALIDATION | Micro_vld_desc |
| VALIDATION FAIL MSG (224) | SELECT THE CODED TEXT DEFINED IN THE CODED TEXT ID UDT (UNLIMITED LENGTH). | Vld_fail_text_id |
| INC TIME (230) | ENTER A NUMERAL TO REPRESENT THE NUMBER OF DAYS A CULTURE MUST BE INCUBATED BEFORE THIS VALIDATION WILL BE EVALUATED. | Inc_time_val |
| EXPECTED RESULTS TEST (1 - 9) (234) | ENTER THE TEST ID THAT IS BEING COMPARED TO VALIDATED TEST. HAVE THE ABILITY TO ENTER UP TO 9 DIFFERENT TESTS AND EXPECTED RESULTS. | Parm_test_no1 (2 - 9) |
| RESULT (1 - 9) (236) | SELECT * (ANY), IN, NI, OR = ENTER THE RESULTS THAT ARE EXPECTED FOR THE TEST. HAVE THE ABILITY TO ENTER UP TO 9 DIFFERENT TESTS AND EXPECTED RESULTS. | Qry_text_val1 (2 - 9) AND rslt_text_val1 (2 - 9) |
| REQ? (238) | SELECT THIS WHEN THE TEST AND THE RESULT IS REQUIRED. HAVE THE ABILITY TO DEFINE UP TO 9 | Req_ind1 (2 - 9) |

| Workcard View - C BLD(PRELIM) | | | | | | | _ □ X |
|---|---|---|---|---|---|---|---|
| Workcard Edit View Options Help | | | | | | | |

400

| 7200 | ▼ ▲ | 09/26/2003 12:33 | ... | BLD ▼ | UNKNOWN DOCTOR | ND |
|---|---|---|---|---|---|---|
| DILLOW RALEIGH | | 342525 | M | 42 | | 09/26/2003 12:33 |

402

Direct Exam    [Add Test] [Enter Result]

| Test ID | Rslt | | | | Rslt Sts | Sts D/T |
|---|---|---|---|---|---|---|
| * GRAM | MANY GRAM NEGATIVE RODS | | | | ENT | 09/26/2 |
| * MEDIA | PERFORMED | | | | ENT | 09/26/2 |

404

520 ▲
[Add/Edit Org] [View Suscept]

Culture Workup  NG  NP  NF  24H  48H  72H  [Enter Result]

| Test Id | Org # | Result | | | | | Test/Biochem RsLt | Tech Notes |
|---|---|---|---|---|---|---|---|---|
| CULT RPT | | | | | | | | |

▼

406

[Comp/Save] [Rel/Save] [Rel/Fin/Save] [Comp/Fin/Save]       [Search] [Close] [Help]

Ready                                                            Micro

514 — (callout to row area)
518 — Direct Exam
516 — Add Test
512 — * marks

FIG. 5d

| Workcard View - C BLD(PRELIM) | | | | | | _ □ × |
|---|---|---|---|---|---|---|
| Workcard  Edit  View  Options  Help | | | | | | |

400

| 7200 | ▶ ▼ ▲ | 09/26/2003 12:33 | ... | BLD | ▶ | UNKNOWN DOCTOR | ND |
|---|---|---|---|---|---|---|---|

402

| DILLOW RALIEGH | 342525 | M | 42 | | 09/26/2003 12:33 |
|---|---|---|---|---|---|

Direct Exam   [Add Test]  [Enter Result]

| Test ID | Rslt | Rslt Sts | Sts D/T |
|---|---|---|---|
| * GRAM | MANY GRAM NEGATIVE RODS | ENT | 09/26/2 |
| * MEDIA | PERFORMED | ENT | 09/26/2 |

404

Culture Workup  [NG] [NP] [NF] [24H] [48H] [72H]  [Enter Result]  [Add/Edit Org]  [View Suscept]

520

| Test Id | Org # | Result | Test/Biochem Rslt | Tech Notes |
|---|---|---|---|---|
| CULT RPT | | | | |
| * ORG ID | 1 | MANY STAPHYLOCOCCUS AUREUS | | |

406

416

[Comp/Save]  [Rel/Save]  [Rel/Fin/Save]  [Comp/Fin/Save]  [Search]  [Close]

420       422         424            426

Ready                                                                [Micro]  [Help]

FIG. 6

| Validation Severity | Validation Test ID/Result 704 | Failed Test ID/Result 706 | User Message 708 | Expected Result 710 | Requires Comment? 712 | Reason to Override 714 |
|---|---|---|---|---|---|---|
| FAIL | GRAM/ MANY GNR | ORG ID/ MANY STAAUR | Gram stain does not match the orgs released. Reconfirm Gram stain. | ORG ID/ IN GNRGRP | N | |

Enter Reason For Override — 720

Do you want to override the validation failure and continue with Release?

Yes 716   No 718   Help

Workcard View - C BLD(PRELIM)

Workcard  Edit  View  Options  Help

7200 | 09/26/2003 12:33 | BLD | UNKNOWN DOCTOR | ND

DILLOW RALIEGH | 342525 | M | 42 | 09/26/2003 12:33

Direct Exam  [Add Test] [Enter Result]

| Test ID | Rslt | Rslt Sts | Sts D/T |
|---|---|---|---|
| MEDIA | PERFORMED | ENT | 09/26/2 |
| GRAM | MANY GRAM NEGATIVE RODS | ENT | 09/26/2 |

Culture Workup  [NG] [NP] [NF] [24H] [48H] [72H]  [Enter Result] [Add/Edit Org] [View Suscept]

| Result | Test/Biochem Rslt | Tech Notes | Rslt Sts |
|---|---|---|---|
| MANY STAPHYLOCOCCUS AUREUS | CAT:P; TUBE:P | | PEND |
| | | | ENT |

[Comp/Save] [Rel/Save] [Rel/Fin/Save] [Comp/Fin/Save]   [Search] [Close] [Help]

Ready    Micro 400, 402, 404, 406, 416, 420, 422, 424, 426, 431, 433

FIG. 9

| Workcard View -C BLD(PRELIM) | | | | | | | _ □ × |
|---|---|---|---|---|---|---|---|
| Workcard  Edit  View  Options  Help | | | | | | | |

400 7200 ▼ ▲ ▼ 09/26/2003 12:33 --- ▼ BLD ▼ UNKNOWN DOCTOR SIG

DILLOW RALIEGH  342525  M  42    09/26/2003 12:33

402 Direct Exam  [Add Test] [Enter Result]

| Test ID | Rslt | | | | | Rslt Sts | Sts D/T |
|---|---|---|---|---|---|---|---|
| MEDIA | PERFORMED | | | | | COMP | 09/26/2 |
| GRAM | MANY GRAM NEGATIVE RODS | | | | | COMP | 09/26/2 |

404 Culture Workup [NG] [NP] [NF] [24H] [48H] [72H] [Enter Result] [Add/Edit Org] [View Suscept]

| Result | Test/Biochem Rslt | Tech Notes | Rslt Sts |
|---|---|---|---|
| MANY STAPHYLOCOCCUS AUREUS | CAT:P; TUBE:P | | PEND |
| | | | COMP |

406

[Comp/Save] [Rel/Save] [Rel/Fin/Save] [Comp/Fin/Save]   [Search] [Close] [Help]

416 ⁀ 420 ⁀ 422 ⁀ 424 ⁀ 426 ⁀

Ready    Micro

| Review Validation Window | | |
|---|---|---|
| Validation Severity | Validation Description | Reason to Override |
| FAIL | Gram Stain with Many or Mod GNR does not have a GNR reported | I re-checked the gram stain and organ |

Do you want to continue with the Review/Finalize action?

Yes — 1002
No — 1004
Help

is a non-provisional application of provisional application Ser. No. 60/455,934 by D. Brumbach et al. filed Mar. 19, 2003.

SYSTEM AND METHOD FOR PROCESSING INFORMATION RELATED TO LABORATORY TESTS AND RESULTS

This is a non-provisional application of provisional application Ser. No. 60/455,934 by D. Brumbach et al. filed Mar. 19, 2003.

TECHNICAL FIELD

The present invention relates to laboratory testing and more particularly to validating test results throughout the testing life-cycle of a clinical culture in a microbiology testing laboratory.

DESCRIPTION OF RELATED ART

Clinical laboratories are tasked with performing tests on clinical cultures to identify organisms which may be causing an infection in a patient. In the normal course of operations, a microbiology laboratory department receives various patient samples collected by physicians. A microbiology technician plates the samples on media and incubate the media. A plated sample is commonly referred to in the art as a "clinical culture". Over the course of time organisms grow on the clinical culture. It is the responsibility of the microbiology technician to identify any organisms (e.g. bacteria, fungus, micro-bacteria, parasite, virus) from the clinical culture which may be causing an infection in the patient and provide any antibiotic information, known to the technician, that may be applicable in treating possible sources of infection.

As is conventional, a laboratory technician analyzes the clinical culture over a period of hours, days or weeks, commonly referred to as the "testing lifecycle" of the clinical culture. Throughout the culture's "testing lifecycle", the technician periodically enters individual test results into a laboratory system as biochemical tests are performed. These individual test results are typically released to the physicians as they occur. Results entered at later stages of the lifecycle should have an expected outcome based on previous results. As one example, if an earlier performed test, such as the Gram Stain test is reported out as many Gram Negative Rods, then in a later performed test, such as an organism ID test, a well-informed technician should expect a Gram Negative Organism as a later test result.

It is incumbent upon the technician to take into consideration the results of earlier tests when entering a later result, so that inconsistent or wrong results are not released to a physician for review.

A drawback of this process is its unpredictability and inconsistency. Specifically, a technician's ability to differentiate between expected and unexpected results depends in large part upon a technician's acquired and remembered knowledge which can vary from technician to technician, his ability to reference charts, manuals and procedures and procedures of supervisory review.

A further drawback of the process is that validation of the culture sample is performed after the culture is finalized (i.e., at the end of the testing lifecycle). This is too late in most instances because any unexpected intermediate results have already been released to a physician for review as they occur. Validation should instead be preferably performed by continuously monitoring and comparing test results as they occur with other culture results throughout the testing life-cycle of the culture, not at the last stage, as is conventional.

A still further drawback is that there is no message capability for informing a technician of what additional steps to take when an unexpected result occurs.

A further drawback is that quantities are not considered during validation, thereby making the validations imprecise.

There are no known systems for processing information related to laboratory tests and results which overcome the aforementioned drawbacks.

SUMMARY OF THE INVENTION

The present invention addresses the need for an improved microbiology validation system. During a culture's "testing lifecycle" in a clinical micro-biology laboratory, numerous results are entered and released over a course of hours, days or weeks. The present invention improves upon this process by providing techniques that consider the results of earlier performed tests when entering results for later performed tests so that inconsistent or wrong results are not released to a physician for review.

In accordance with one aspect of the present invention, a method for processing information related to laboratory tests and results comprises: an interface processor that receives user entered data identifying a laboratory test result of a patient and an expected result of the laboratory test. A validation processor compares the laboratory test result with the expected test result and identifies a failure condition in the case where the laboratory test result fails to match the expected test result. A result processor generates an alert message to the user informing the user of the failure condition.

BRIEF DESCRIPTION OF THE DRAWINGS

Referring now to the drawings in which like reference numbers represent corresponding parts throughout, where:

FIG. 3 is an exemplary listing of those micro-validation parameters included in the top portion of the UDT of FIG. 2; and FIGS. 4–10 are computer display image windows of various user interface screens in accordance with aspects of the invention.

DETAILED DESCRIPTION OF THE INVENTION

Figure 1:
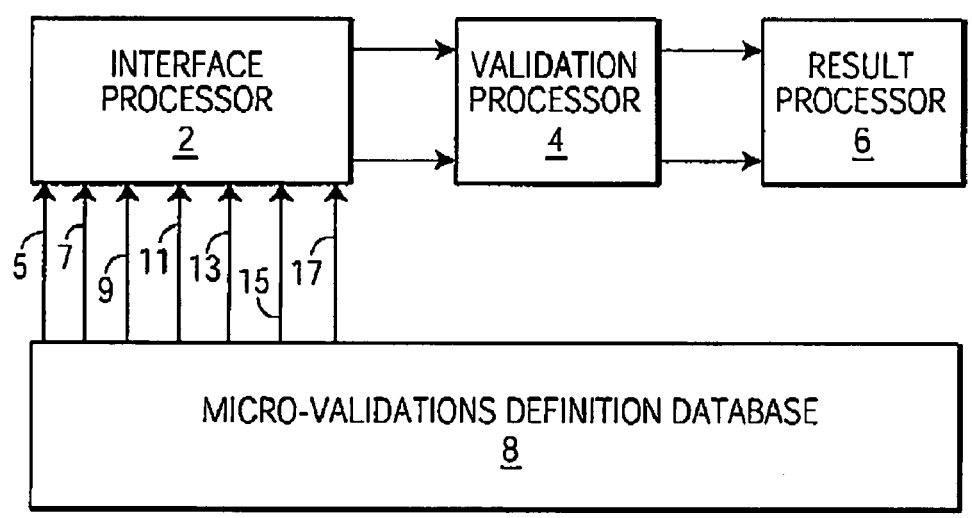
FIG. 1 illustrates one embodiment of a microbiology validation system for processing information related to laboratory tests/results.

The system of the invention is suitable for use in pharmacy and radiology information systems and enables a user to define simple or complex result validation processes and messages. The system has particular application to a hospital laboratory setting enabling the efficient and accurate analysis of a culture. The analysis of a culture may include reporting various microbe types which may include a bacteria, a fungi, a parasite and a virus. It is in this context that the present invention is described. A processor as used herein is a device and/or set of machine-readable instructions for performing task. A processor comprises any one or combination of hardware, firmware, and/or software. A processor acts upon information by manipulating, analyzing, modifying, converting, transmitting the information for use by an executable procedure, an information device, and/or routing the information to an output device. A processor may use the capabilities of a controller.

The system of the invention provides a number of specific advantages over prior art systems including performing validations of test cultures by continuously monitoring and comparing test results as they occur with previously obtained test results throughout the lifecycle of a culture. A further advantage provided by the invention is a capability to monitor test results that are entered throughout the lifecycle of a culture. The invention also advantageously considers specific quantities when defining expected results and alerts a user of unexpected results prior to their release to a physician for review. A still further advantage allows a user to define who can override a validation failure and in a related aspect, allows the entry of an override comment directly from a validation failure window. With specific regard to messaging, the invention provides the user with the ability to define user messages and allows a user to customize the system to provide reminders to other personnel. The invention also includes a failure management report which lists those tests which have been overridden by a lab technician. With regard to expected and actual test results, the invention provides a validation failure window that displays both an expected test result value and an actual test result value that caused the validation failure and allows a user to define or construct what constitutes an expected result rather than defining exceptions to the expected result.

The disclosed elements to be described herein may be comprised of hardware portions (e.g., discrete electronic circuitry), software portions (e.g., computer programming), or any combination thereof. The system according to the invention may be implemented on any suitable computer running either UNIX, Windows NT, Windows 2000 or Windows XP. Obviously, as technology changes, other computers and/or operating systems may be preferable in the future. The system as disclosed herein can be implemented by a programmer, using commercially available development tools.

One of skill in the art can appreciate that the display image windows illustrated in the figures for the embodiments of the present invention represent one possible arrangement and that other arrangements may be used which may include several image windows in place of one image window illustrated in the figures, or conversely one image window to represent several image windows, or different image window arrangements.

The micro-biology validation system is described in a non-limiting context of testing cultures in a clinical micro-biology laboratory.

The present invention may be more fully understood with reference to FIG. 1, which illustrates the microbiology validation system 100 in accordance with one embodiment. The micro-biology validation system 100 includes, for example, an interface processor 2, a validation processor 4, a result processor 6 and a micro-validation definitions database 8. The micro-validation definitions database 8 stores micro-validation definitions which define the expected test results for those laboratory tests required to be validated, to be described further below.

The micro-biology validation system 100, in the exemplary embodiment, is comprised of one or more software modules integrated within an external computer system such as a hospital laboratory information system (LIS).

The invention operates in two-stages, a pre-configuration stage and an operational stage. At the pre-configuration stage, a user makes a determination regarding which tests from among the plurality of tests to be performed on a clinical culture require validation. Validation, as defined herein, involves looking for unexpected test results based on user supplied pre-defined expected results. For those tests identified by the user requiring validation, the user creates one or more micro-validation definitions which define an expected result. Once created, the micro-validation definitions are stored in a micro-validations definition database 8 for later recall during the operational stage for comparison with actual test results to make a determination regarding the validity or invalidity of a test requiring validation. The two stages of the process, pre-configuration and processing are described in greater detail as follows.

At the pre-configuration stage, a user (customer) first decides which tests require validation from among those laboratory tests to be performed on a particular clinical culture. In the illustrative example to follow, reference is made to a blood clinical culture. In the specific case of a blood clinical culture, one test typically performed on the blood culture sample requiring validation is a GRAM test. To validate the GRAM test, the user completes a user defined template (UDT) 200 of FIG. 2, including data such as: an expected GRAM test result, a plurality of pre-conditions, and one or more further defined tests and their expected results, where the further defined test's expected results are supplied by a user in consideration of the earlier performed GRAM test and its expected result.

Figure 2:
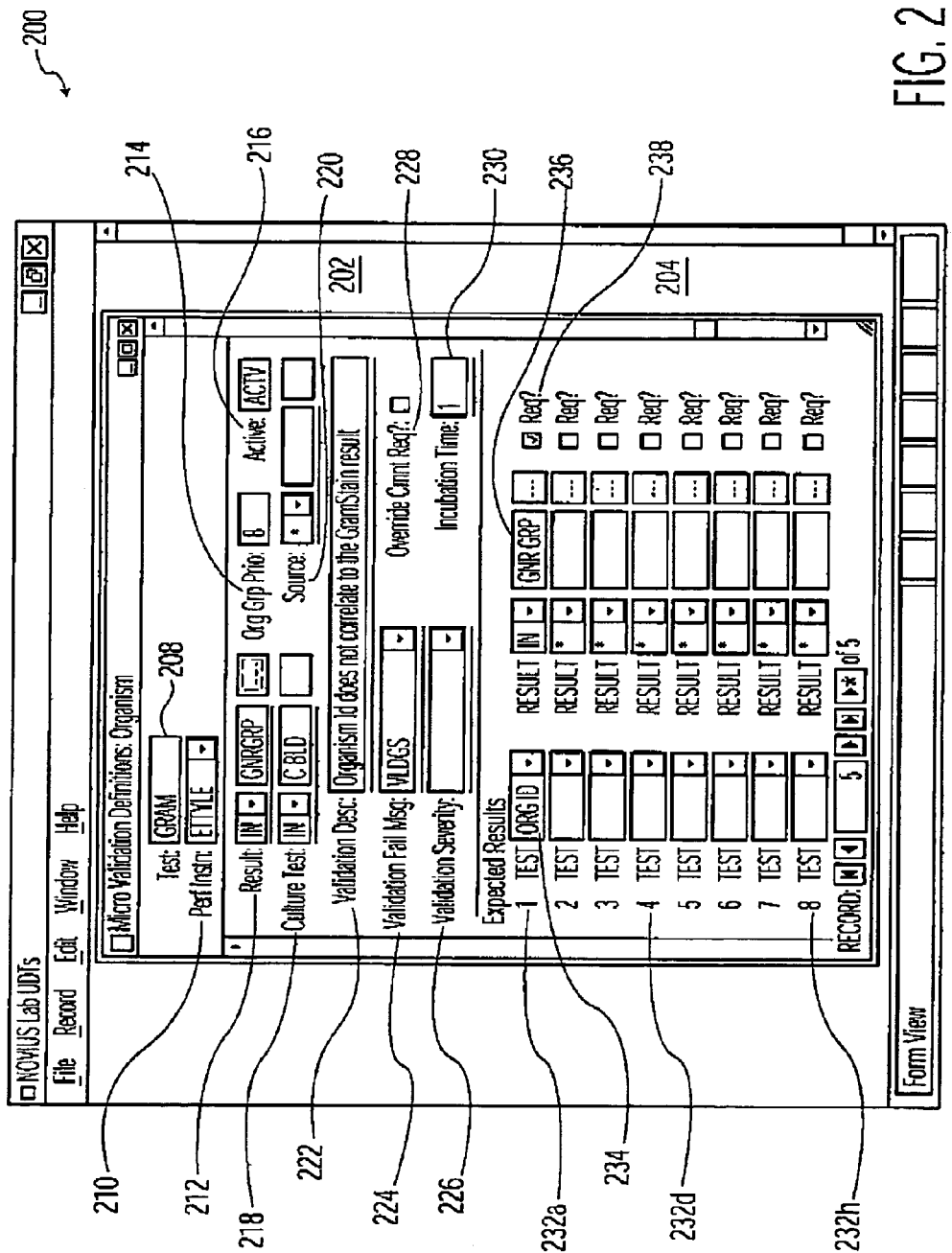
FIG. 2 is an exemplary display image window illustrating a micro validation user defined template (UDT) for constructing a micro-validation definition.

A user defines an expected result for user identified tests requiring validation by completing one or more user defined templates (UDTs), such as the exemplary UDT shown in FIG. 2.

FIG. 2 is an exemplary display image window illustrating one embodiment of a UDT template 200. The UDT 200 template, once completed by the user, is stored as a micro-validation definition of the expected result for a particular test requiring validation. Micro-validation definitions are created for those tests requiring validation, as determined by the user.

As stated above, the creation of a micro-validation definition for a test to be validated requires that the user identify the test to be validated along with its expected result, supply data including pre-conditions and identify any further tests and their respective expected results in consideration of the test to be validated. With regard to any further tests, a user has the option of requiring or not requiring that the actual test result matches an expected test result. This option is provided by checking or not checking the "Req?" entry box 238, associated with the line entry identifying the further defined test on UDT 200 during pre-configuration.

One example of a pre-condition of UDT 200 is the "Incubation Time" field 230 shown in the top portion 202 of UDT 200. In the instant example, the user has entered a value of "1", representing 1 day for the "Incubation Time" field. The user has determined that a necessary pre-condition for validating the "GRAM" test 208 is an incubation time equal to or greater than one day.

Determining whether the incubation time pre-condition is satisfied is carried out by system 100 as follows. Validation processor 4 is configured to check the current date that the test result is observed with the start date of the culture to determine if the incubation time is at least 1 day. If the incubation time is determined to be less than 1 day, the pre-condition is not satisfied and micro-validation is not performed for the "GRAM" test 208.

Upon completing the UDT 200 for a particular test to be validated, the micro-validation parameters provided by the user to fill out the UDT template 200 are stored in the micro-validation database 8 as a single record. The record is comprised of the various pre-condition parameter values and further defined tests and their associated expected values. The micro-validation record is later recalled at various times during the processing stage to perform test validation.

The exemplary UDT 200 of FIG. 2 is shown to be divided into a top portion 202 and a bottom portion 204. The top portion 202 includes fields such as a test description field, i.e., "Test" 208 identifying a laboratory test to be validated, performing institution "Perf Instn" 210, "result" 212, organization group priority ("Org Grp Prio") 214, activation ("Active") 216, "Culture Test" 218, "Source" 220, validation description ("Validation Desc.") 222, validation failure message ("Validation Fail Msg.") 224, "Validation Severity" 226, override comment required ("Override Cmnt Req?") 228, and "Incubation Time" 230. From among the aforementioned fields, the fields that define pre-conditions comprise fields 208, 212, 214, 216, 218, 220 and 230 of FIG. 2.

The bottom portion 204 of UDT 200 includes a number of entry lines 232a–h for allowing the user to define further laboratory tests 234 and their associated expected test results 236 for the purpose of validating or invalidating the test requiring validation (e.g., GRAM test 208).

The "Req?" entry box 238 when checked, requires that a further laboratory test, e.g. ORG ID 234, is to be considered as a confirmatory test when performing validation. In the case where two or more further laboratory tests 234 are utilized as confirmatory tests in the bottom portion 204 of UDT 200, then a failure condition occurs whenever at least one confirmatory tests actual result fails to match its expected result.

Table I of FIG. 3 describes the micro-validation parameters illustrated in the top portion 202 of UDT 200 of FIG. 2. The first column 30 of Table I identifies the various micro-validation parameters 208–238. The second column 32 provides a brief description of the micro-validation parameters 208–238 of the first column. For example, it is shown that for the micro-validation parameter "validation severity" 226, a user has the option of selecting one of three messages to be displayed when an unexpected test result occurs, i.e., "INFO", "WARN", or "FAIL". The choice may be different for the different micro-validation tests to be performed. The third column 34 describes how the micro-validation parameters may be stored in micro-validation database 8 in one embodiment.

For the laboratory tests requiring validation, one or more UDTs 200 per test to be validated are completed in the manner described above during the pre-processing stage. When the user completes a UDT 200 for those tests requiring validation, the pre-configuration stage is considered complete.

The processing stage follows the pre-configuration stage and involves the life-cycle testing of a clinical culture over a period of hours, days or weeks. Processing of a culture starts with a physician determining that a culture needs to be obtained from a patient. A culture is obtained from the patient and delivered to the microbiology laboratory. Upon making a determination that a culture is appropriate for the body site, the laboratory accessions the culture into the laboratory information system (LIS), as is conventional.

Throughout the processing stage a laboratory technician performs tests and records results pertaining to a culture under consideration. To carry out the necessary operations involved in the life-cycle testing of a culture, the technician interfaces with the system of the invention via a user interface, referred to herein as a "work-card" for processing information related to laboratory tests and results.

Figure 4:
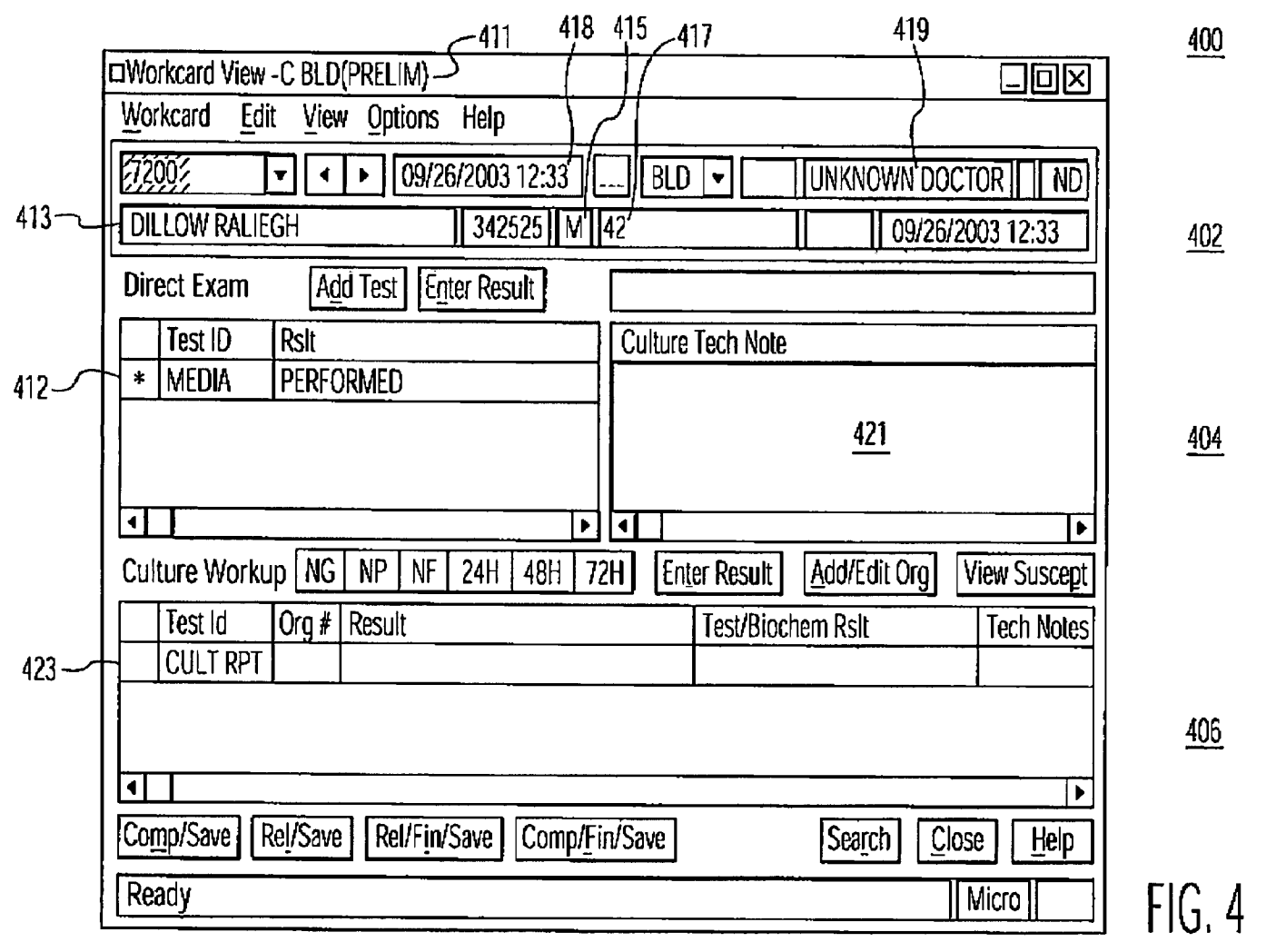

FIG. 4 is a display image window of one embodiment of a so-called "work-card" 400 which is called up on a work-screen by the technician at the outset of the processing stage.

By way of example, the micro work-card 400 of FIG. 4 is shown to a technician in response to the technician calling up a blood culture for a patient. It is to be appreciated that a work-card of a "blood culture" type (C BLD) 411 represents one of a wide variety of culture types that a technician may elect to call up. Other culture types that may be called up by a technician may include, for example, a wound culture, sputum culture, urine culture and so on.

Work-card 400 is the display user interface used by a laboratory bench technician throughout the testing lifecycle of a culture that allows the technician to enter, display, review, accept and reject test results as they occur.

Work-card 400 is divided into three regions, a first (upper) region 402 including a title field. 411, "C BLD (PRELIM)" and various patient demographics, such as name 413—"Dillow, Raliegh", gender 415—"M", age 417—"42", attending physician 419—"UNKOWN DOCTOR". The title field 411, e.g., "C BLD (PRELIM)" identifies the work-card 400 as a blood culture type of work-card.

The second (middle) region 404 of work-card 400 is labeled "Direct Exam" and represents an area for displaying the tests that can be performed directly on the specimen culture. In the instant example, entry line 412 shows under the title "Test ID", MEDIA and under the title "Rslt", PERFORMED. The MEDIA test is a user defined test that is automatically part of the Blood Culture group test. It is noted that some users do not define this test. Of the users who do define the MEDIA test, most users have the test automatically resulted with a "PERFORMED" status for any number of reasons including auditing, inventory, system and internal reasons. Alternatively, a user can manually enter a result for the MEDIA test. An indication to a lab technician that a blood culture has been inoculated and that life-cycle testing has begun is provided by seeing a result in the "Rslt" field, e.g., PERFORMED, in combination with an entry in the Plated date/time field 418, e.g., "Sep. 26, 2003". Also shown in the second region 404 is a "Culture Tech Note" field 421 which is used for non-reportable information that may be shared among laboratory personnel using the work-card 400.

The third (lower) region 406 of work-card 400 is labeled "Culture Workshop" and represents an area of the work-card 400 for displaying the status of non-direct tests performed on the culture specimen. The "CULT RPT" test indicated at entry line 423 is a standard test performed as part of the blood culture group tests. Entry line 423 is automatically displayed whenever a work-card of the blood culture type is brought up by a lab technician.

It is to be appreciated that the layout of work-card 400 represents one embodiment which is representative of the paper legacy system from which it is derived. Other layouts are within the contemplation of the invention.

FIG. 5a is a display image window of the work-card 400 of FIG. 4 in the normal progression of preparing the blood culture. FIG. 5a illustrates the same data shown in FIG. 4 and additionally includes entry-line 512 in the "Direct Exam" region 404 of the work-card 400 indicating that the technician has performed a gram stain test, i.e., "GRAM", and observed its corresponding test result, i.e., "MANY GRAM NEGATIVE RODS". Entry-line 512 further shows that the result has been entered, i.e., see "ENT" 514 under the heading "Rslt Sts" into the system 100. ENT status is indicative of a result that has been entered into the system but not yet released to a physician for review.

As is well known to those knowledgeable in the testing arts, preparatory steps for performing a gram stain test include inoculating the culture sample onto an appropriate media, and a microscopic slide and placing the inoculated media in an incubator for overnight incubation. Subsequent to the incubation period, the technician performs the Gram Stain test and enters the test result into the system 100.

The process of entering a test result is now described with reference to FIGS. 1 and 5 and Table II below.

With reference first to FIG. 1, as tests are performed, such as the gram stain test, results are entered into the system 100. Tests are entered via interface processor 2 which is configured to receive input data, including test result data, at different time stages throughout the testing life-cycle of the culture.

Table II illustrates the various types of data which may be received by the interface processor 2 of FIG. 1. The first column is a description of the various data types and the second column is a description of specific examples of those data types as used in the instant example.

TABLE II

| Generalized input | Exemplary input |
| --- | --- |
| a FIRST laboratory test identifier 5: identifies a laboratory test requiring validation processing, | GRAM test |
| An EXPECTED first laboratory test result 7 | GNRGRP - i.e., MANY GRAM NEGATIVE RODS |
| An ACTUAL first laboratory test result 9 | GNRGRP- i.e., MANY GRAM NEGATIVE RODS<br>* Note: the actual result 9 matches the expected result 7. |
| a FURTHER laboratory test identifier 11: identifying a further laboratory test for validating the first laboratory test | ORG ID |
| An EXPECTED FURTHER laboratory test result 13 | GNRGRP |
| An ACTUAL FURTHER laboratory test result 15 | *Staphlococcus Aurues*<br>* Note: the actual further test result 15 does not match expected further laboratory test result 13. |

Validation processor 4 performs validation processing by comparing an actual laboratory test result 9 (row 3 of Table II) with an expected test result 7 (row 2 of Table II) for the test requiring validation, e.g. Gram test 208 of FIG. 2 and for the further performed tests which are performed at a later stage to validate or invalidate the test to be validated, e.g., Gram test 208. In FIG. 2 a single further performed test is shown for the purpose of validating the Gram test 208. The further performed test shown is the ORG ID test 234 with its expected result, i.e., GNRGRP 236. A failure condition is identified when an actual laboratory test result 9 (row 3 of Table II) fails to match its expected result 7 (row 2 of Table II) for the test to be validated, e.g., the Gram test 208. A failure condition is also identified when a further performed actual test result 15 (row 6 of Table II) fails to match its expected test result 13 (row 5 of Table II). In those cases where a failure condition occurs, the result processor 6 generates an alert message to the user.

An expected result can be expressed in a number of ways. Some common expressions may be recited by indicating, for example, that the culture is "resistant" to a test compound, or "sensitive" to a test compound. The test result can otherwise be simply expressed as having either a "positive" or "negative" test result.

It should be appreciated that an expected result can also be expressed as a qualitative description of a quantity, as recited in the instant example (GRNGRP=many gram negative rods) where the term "many" represents the qualitative description of the quantity "gram negative rods". Other qualitative descriptors used by the present invention include, but are not limited to, "few", "resistant", "sensitive", "positive" and "negative").

Some examples of the qualitative descriptors are as follows. If the test to be validated is, for example, an ORG ID test and its test result is "*Klebsiella pneumoniae*, then a confirmatory test such as Ampicillin (AM) has an expected result of "resistant". If the ORG ID test result is "*Staphylococcus aureus*", then a Vancomycin (VA) confirmatory test has an expected result of "sensitive". If the ORG ID test result is "*Staphylococcus*", then a Catalase confirmatory test (CAT) has an expected result of "positive". If the ORG ID test result is "Streptococcus", then a Catalase confirmatory test has an expected result of "negative".

Figure 5B:
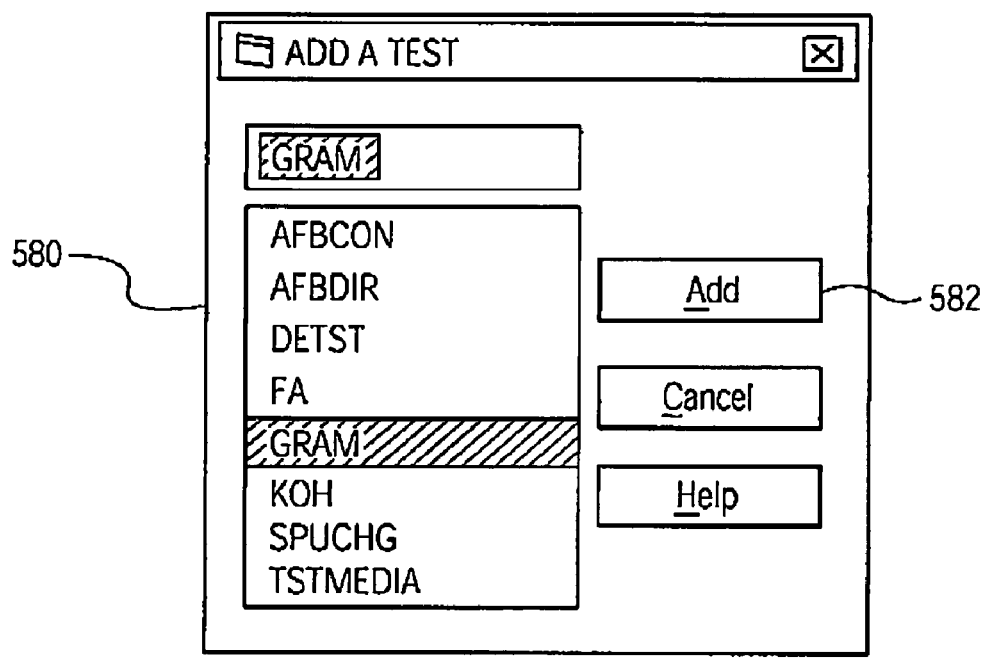

Another example of using a qualitative quantity indicator would be in the case where a Sputum Culture is used as a confirmatory test (see 218 of FIG. 2) having an expected result of "Many" gram negative rods (GNRGRP). With reference again to FIG. 5*a*, entering a test identifier and its corresponding test result into system 100 of the invention involves the acts of clicking on the "Add Test" icon 516 of work-card 400 of FIG. 5*a*. In response, the pop-up window 550 of FIG. 5*b* is displayed to the technician. Area 580 of pop-up window 550 lists the various tests that can be added by the technician for the blood culture example. In the instant example, the technician would highlight the "GRAM" test and click on the "Add" icon 582 causing the pop-up window 550 to disappear and entry-line 512 to appear on work-card 400 of FIG. 5*a*.

Figure 5C:
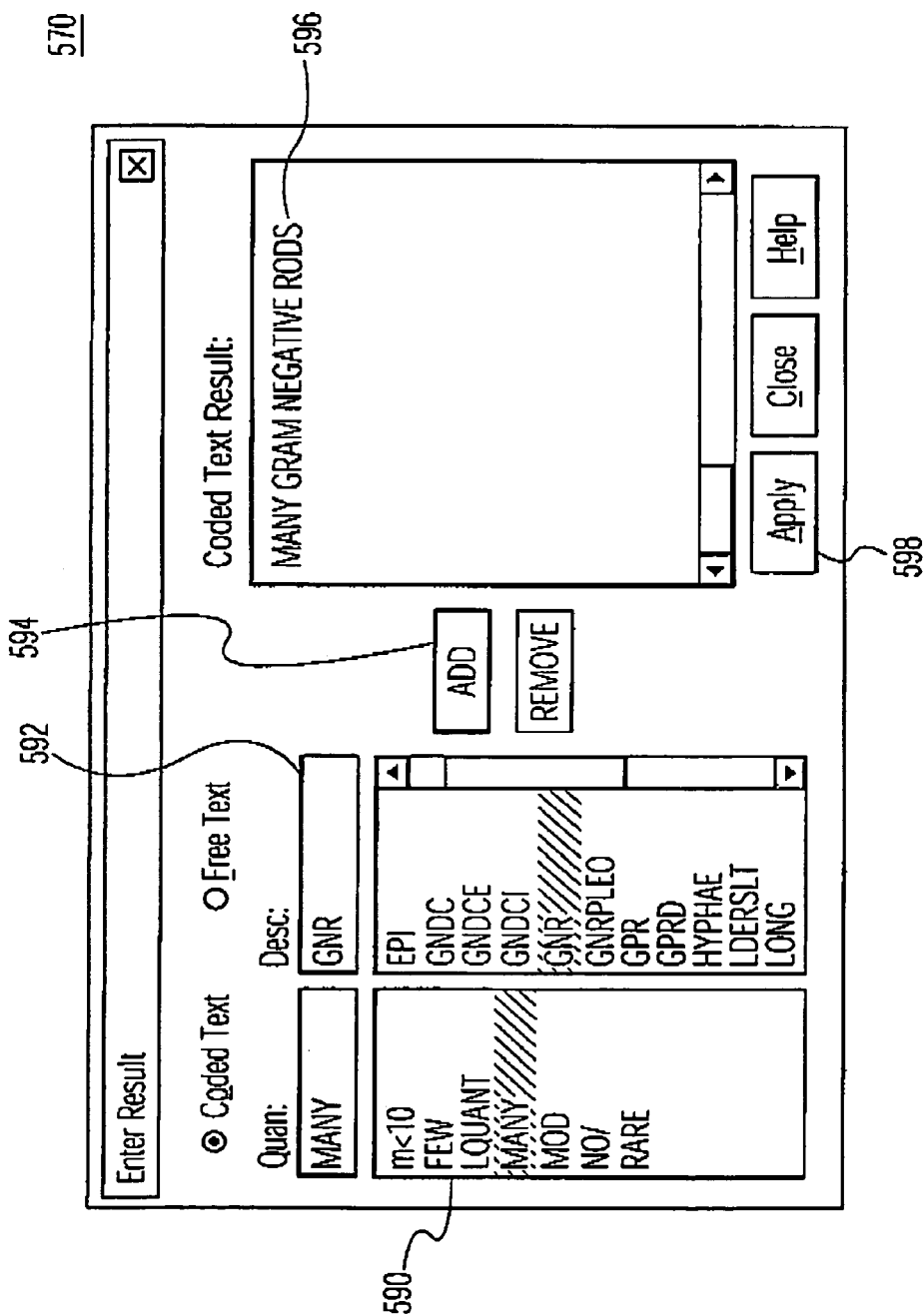

The test result for the GRAM test, as observed by the technician, is then entered into system 100 by pressing the "Enter Result" icon 518 of work-card 400 of FIG. 5*a*. In response, pop-up window 570 of FIG. 5*c* is displayed to the technician. Pop-up window 570 includes a quantity menu 590 and a description menu 592 wherein the quantity menu 590 lists a menu of test result quantities, and a description menu 592 lists a menu of test result descriptions. In the instant example, for a "many gram negative rods" result for the GRAM STAIN test, the technician would select "MANY" from the quantity menu 590 and "GNR" from the description menu 592. Upon clicking on the "Add" icon 594, the coded text result "MANY GRAM NEGATIVE RODS" is displayed" in the coded text result region 596 of the pop-up window 570 thus providing the technician with a further opportunity to revise the choice made prior to clicking on the "Apply" icon 598. Subsequent to clicking on the "Apply" icon 598, the entered test result appears on line 512 of the work-card 400 of FIG. 5*a* as 'MANY GRAM NEGATIVE RODS'.

Next, in the normal course of testing a blood culture sample, at a later stage, the technician receives the blood culture sample with organisms grown on it. A number of bio-chemical tests are performed and the results entered into system 100 via work-card 400. In the instant example, the bio-chemical tests performed on the blood culture sample result in a determination of "Many Staph Aurues". The technician enters the test results for the later performed biochemical tests by clicking on the "Add/Edit Org" button 520 of the work-card 400 of FIG. 5*a* to enter the organism tests/test results and an organism identification.

Figure 5D:
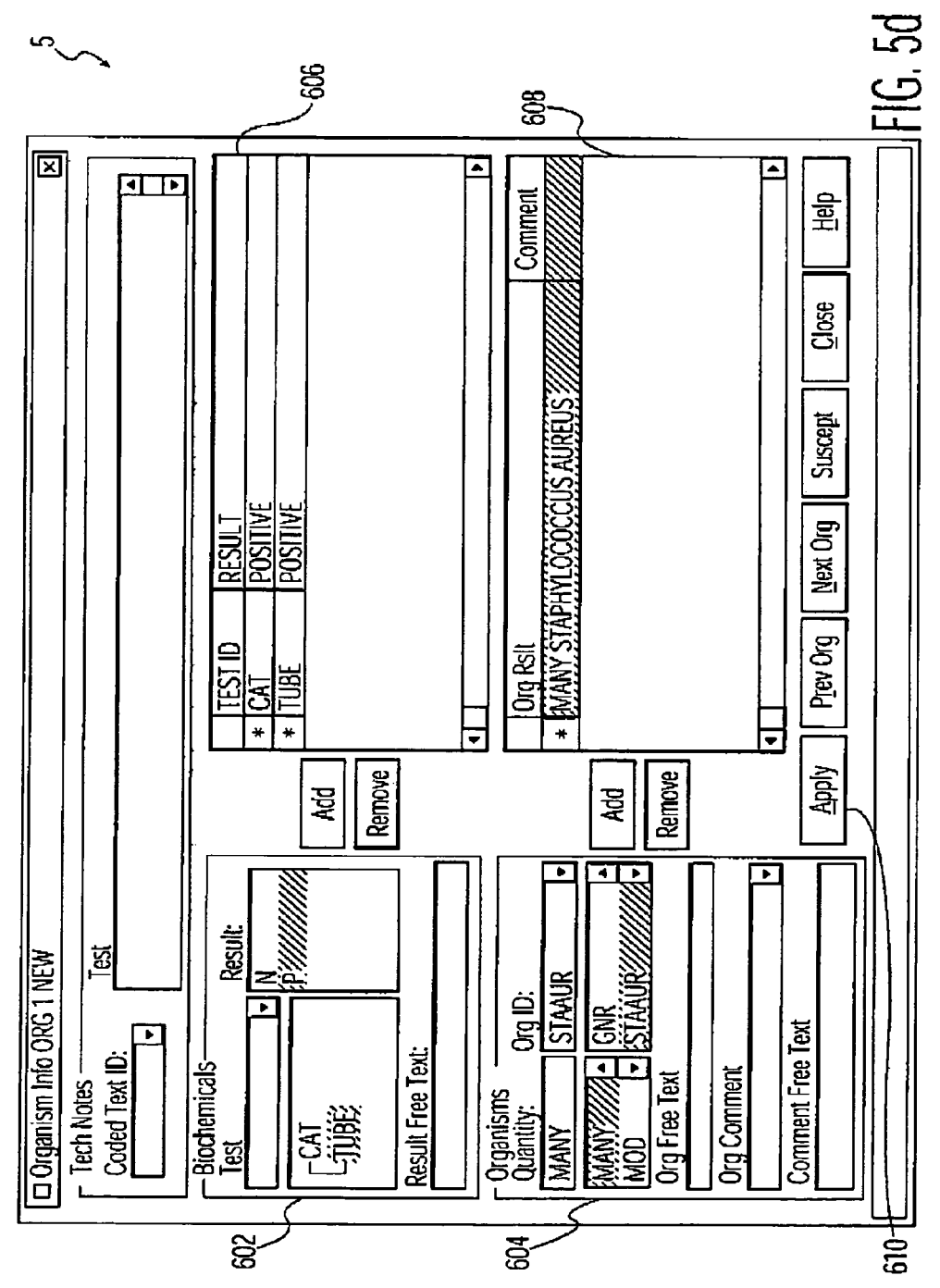

FIG. 5*d* is a pop-up window 580 that is displayed to a technician in response to the technician clicking on the "Add/Edit Org" button 520 of FIG. 5*a*. Individual biochemical tests are entered in area 602. As the results are entered, they appear in the upper right-hand portion 606 of the pop-up window. Organism quantities and identifications are entered in region 604, the results of which appear in the lower right-hand region 608 of the pop-up window.

In the illustrative example, the technician performs two bio-chemical tests, a catalyse test, "CAT" and a tube coagulase test, "TUBE". Both test results are determined by the technician to be positive resulting in an organism identification of "Many *Staphlococcus Aurues*". The technician clicks on the "Apply" icon 610 to accept the results.

FIG. 6 is a display image window of work-card 400 in response to the technician clicking on the "Apply" icon 610 in FIG. 5*d*. The display image window includes new entry line 416 in region 406 which represents information about the bio-chemical tests performed and the organism identification. It is well known to those in the art that an organism identification of "Many *Staph Aureus*" is not a type of Gram Negative Rod as expected. The expected result is "GNR-GRP" 236 (see FIG. 2). If the incorrect result is attempted to be released to a physician for review, it would result in a validation failure.

At this point it is instructive to describe the various ways in which a result can be released to a physician for review. In general, three status types exist: "Enter status", "Review Status" and "Release Status". "Enter Status" defines the case where a technician enters a test result into the system 100 but does not make that result available to the floor. "Review Status" defines the case where a supervisor reviews a test result prior to allowing it to be entered to the floor and "Release Status" defines the case where the result is both entered into the system 100 and released to a physician for review. The status conditions described above are implemented in the work-card 400 via four icons.

With reference now to FIG. 6, four icons are shown on the lower left-hand portion of work-card 400, i.e., "Comp/Save" 420, "Rel/Save" 422, "Rel/Fin/Save" 424 and "Comp/Fin/Save" 426. Various options are provided here to accommodate different laboratory policies and levels of technician professionalism for the review of results.

The "Comp/Save" icon 420 is used to save a test result when the test result has been reviewed by either a supervisor or a lab technician with appropriate security credentials. The review may take place on-line or by using work-card 400 printouts. It is assumed that additional tests are performed subsequent to saving the instant result. In other words, the end of the culture's testing lifecycle has not been reached. Subsequent to the review, the test result is released to a physician for review.

The "Rel/Save" icon 422 is applicable to those cases where a lab technician does not possess appropriate credentials and a supervisory review is mandated. It is assumed that additional tests are performed subsequent to saving the instant result. In other words, the end of the culture's testing lifecycle has not been reached.

The Comp/Fin/Save" icon 424 is applicable at the end of a culture's testing lifecycle identical and includes the features described above for the "Comp/Save" icon. In addition to the afore-mentioned features, the Comp/Fin/Save" icon 424 saves any updated/unsaved data to the database 8. At this point in time, the culture status changes from "preliminary" to "final" (see "C BLD (PRELIM)" 411 of FIG. 4).

The Rel/Fin/Save icon 426 may also be used to finalize the lifecycle testing of the culture, however, in this case the technician needs to perform an additional step. Specifically, the technician is required to manually perform a REVIEW action (located under the work-card 400 menu option).

In the instant example, the technician attempts to release the laboratory test result, i.e., "Many *Staph Aureus*" for the organism identification test, i.e., "ORG ID" 234. In this case, the actual test result does not match the expected test result, i.e., "Gram Negative Rod" 236. Therefore, attempting to release the actual laboratory test result results in a validation failure.

While a technician would not, under normal circumstances, attempt to release a failed test, for purposes of illustrating aspects of the invention, it is assumed that the technician releases the laboratory test result, i.e., "Many *Staph Aureus*", by either pressing the "Comp/Save" icon 420 or the "Rel/Save" icon 422.

FIG. 7*a* is a display image window of a failure validation screen 700 that is displayed to the technician when attempting to release, a failed result. The failure validation screen 700 provides the technician with an opportunity to review the detected failure and decide whether or not to override the failure and release the result to a physician.

Independent of the system of the invention, in accordance with pre-existing security measures incorporated into a laboratory information system, each technician is initially provided with a security access status that allows the technician to perform certain functions within the overall laboratory system. One aspect of this security access status allows a technician to override any validation failure whose validation security level status is determined to be either "Informational" or "Warning". In the case where the validation security level status is "Failure", a technician may override the failure if the technician's security status is "validation". An authorization processor, incorporated as part of the laboratory information system, is used to determine the technician's security status and allow or deny the override. With reference to FIG. 7*a*, a technician can override a failure by pressing the "Yes" icon 716 when the technician's status is "validation".

The failure validation screen 700 is shown to include a number of columns including a first column entitled "Validation Severity" 702 for describing the validation failure severity of the failed test. In the illustrative example, the validation severity is shown as "FAIL". As stated above, the validation severity level is set during the pre-processing stage via UDT 200. Validation severity can be set as one of "INFO", "WARN" or "FAIL".

The second column of the failure validation screen 700 is entitled "Validated TestID/Result" 704 identifying a test to be validated and its expected result. In the instant example, the "TestID/Result" 704 is the GRAM STAIN test 208 (see FIG. 2) and the expected result is many gram negative rods "MANY GNR" 212 (see FIG. 2).

The third column of the failure validation screen 700 is entitled "Failed TestID/Result" 706 identifying a test performed at a later stage of the testing lifecycle of the culture and its observed (actual) result. In the instant example, the ORG ID test is performed at a later stage as a confirmatory test for the earlier performed ORG ID test. As shown in 706, the actual test result for the ORG ID test is "MANY STAAUR". Recall that when constructing the micro-validation definition of the Gram test 208, the ORG ID test 234 of FIG. 2 is included as a test to be later performed as a validation or confirmatory test, as shown on entry line 232*a* of FIG. 2 along with its expected result, GNRGP 236 of FIG. 2 also shown in the fifth column 710 of FIG. 7*a*. Upon performing the ORG ID test, its actual or observed result, i.e., "MANY STAUUR" 706 is different from its expected test result GNRGRP 236 thereby invalidating the earlier performed GRAM STAIN test 208.

The fourth column of the failure validation screen 700 is entitled "User Message" 708 providing an indication to the technician that the earlier performed test/result 704 to be validated, in this instance, does not match the actual test/result 706. The message shown includes a user prompt recommending that the technician reconfirm the earlier performed test. The message prompts may also include, for example, prompts directing the technician to perform another predetermined laboratory test, prompts directing the technician to repeat a test, prompts providing a user predetermined message and prompts identifying an actual test result and an expected test result.

The fifth column of the failure validation screen 700 is entitled "Expected Result" 710 identifying the later performed test and its associated expected result. In the instant example, an expected result for the later performed "ORG ID" test is "GNRGRP", i.e., gram negative rods.

The sixth column of the failure validation screen 700 is entitled "Requires Comment" 712 and displays an "Y" (yes) or "N" (no) to provide a quick indication to the technician if the validation requires a reason for override or not in order for the validation to be overridden. If the column displays "Y" and the technician presses the YES icon 716 (and there is no reason for override entered, see 714) a message is displayed to the technician to enter a reason for override. This column can potentially save the technician time, by displaying to the technician those cases where a reason is to be entered prior to a validation override. In the instant example, an "N" (no) is shown at 712, indicating no reason for override is required, so the YES icon 716 can be pressed and the validation is overridden without a reason entered at 714.

The seventh column of the failure validation screen 700 is entitled "Reason to Override" 714 and provides a display of any "reason for override" that may have been entered. The technician has an opportunity to provide a brief description for overriding the validation failure. Text can be entered for this override field by pressing the "Enter Reason For Override" icon 720 at the top left portion of the Failure Validation Window of FIG. 7a. The "reason for override" is incorporated into a validation review record that is reviewable by a supervisor. The validation review record is defined below in connection with FIG. 10.

Figure 7B:
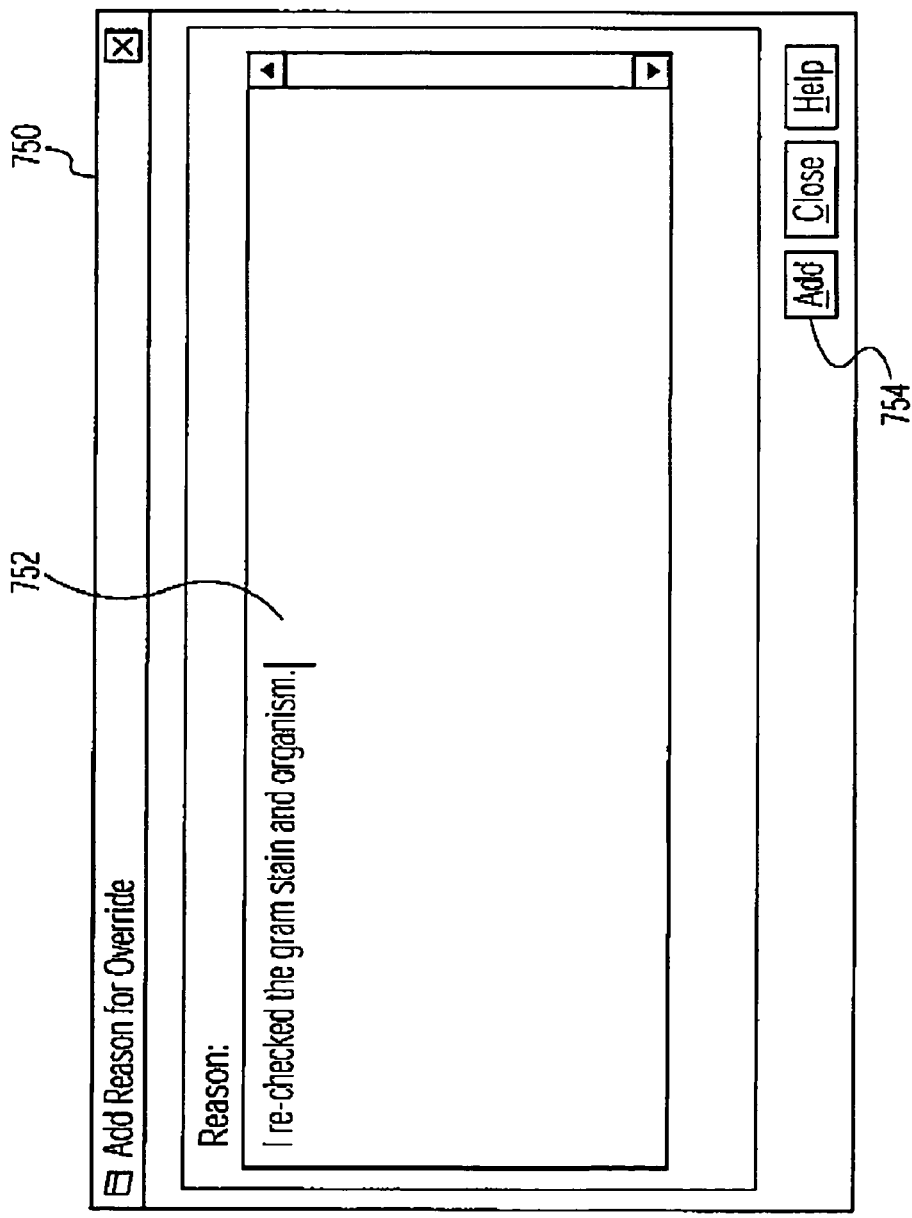

FIG. 7b is a display image window of a pop-up window 750 shown to the technician in response to the technician pressing the "Enter Reason For Override" icon 720 in FIG. 7a. The pop-up window 750 includes a text entry field 752 for providing an override reason. Upon clicking on the "Add" icon 754, the text is included in the text field of the validation window of FIG. 7a at 714.

The technician has the option of pressing the "Yes" icon 716 of FIG. 7a to accept (override) the validation failure and release the later performed test result to a physician or the "No" icon 718 of FIG. 7a and not release the test result to a physician. It is noted that overriding a validation failure by pressing the "Yes" icon 716 results in the override being included in a management report, reviewable by a supervisor.

FIG. 8 is a display image window of work-card 400 shown to the technician in response to the technician pressing the "No" icon 718 at the failure validation screen of FIG. 7a. When a technician presses the "No" icon 718 and chooses to not accept the test results for a validation failure, the technician has a number of options including re-reading the gram stain again, entering a new result for the gram stain or going back to the original blood culture and starting again. Selecting the "No" icon 718 prevents the test result from being released to a physician for review. It is noted that the entry line 416 of FIG. 8 (shown scrolled to the right relative to that shown in FIG. 6) includes an ENT entry 433 under the heading "Rslt Sts". This indicates that the result is saved to the database 8 but not yet released to a physician for review. Entry line 416 further shows the biochemical tests performed on the organism and the associated results 431. In the illustrative example, two biochemical tests performed on the blood culture are shown, i.e., the CAT test and the TUBE test, both having a positive P result. It should be appreciated that the two biochemical tests, CAT and TUBE, can also be validated, if the user desires, in the manner described above. In other words, a test used to validate an earlier performed test may itself be validated by a later performed test. It is noted, however, that to validate any test, a UDT 200 is required to be filled out during the pre-processing stage.

FIG. 9 is a display image window of work-card 400 shown to the technician in response to the technician pressing the "Yes" icon 716 at the failure validation screen of FIG. 7a. Selecting the "Yes" icon 718 releases the test result to the physician. It is noted that the entry line 416 of FIG. 8 (shown scrolled to the right relative to the same line shown in FIG. 6) includes a COMP entry 417 under the heading "Rslt Sts". The COMP entry indicates that the result has been saved to the database and released to a physician for review.

In the instant example, the "ORG ID" test is performed as the last validating or confirmatory test for the blood culture under consideration. Therefore, subsequent to performing the ORG ID test and recording the result, the technician presses the "Rel/Fin/Save" icon 424 to finalize the life-cycle testing of the blood culture.

FIG. 10 is a display image window of a Review Validation Window 1000. The review validation window 1000 is available from a drop down list on the work-card 400 of FIG. 9. In the case where a culture had one or more overridden validations, a supervisor has the ability to review a list of overridden failure validations and has the option to continue with the process of finalizing the culture by pressing the "Yes" icon 1002 or otherwise decide to not finalize the process by pressing the "No" icon 1004.

Although this invention has been described with reference to particular embodiments, it should be appreciated that many variations can be resorted to without departing from the spirit and scope of this invention as set forth in the appended claims. The specification and drawings are accordingly to be regarded in an illustrative manner and are not intended to limit the scope of the appended claims.

What is claimed is:

1. A system for processing information related to laboratory tests and results, comprising:

an interface processor for receiving user entered data identifying a laboratory test result of a patient specimen culture and for receiving user entered data identifying an expected result of said laboratory test and data identifying a validation pre-condition;

a validation processor for employing one or more user determined validation pre-conditions in comparing said laboratory test result with said expected test result and identifying a first failure condition in response to said laboratory test result failing to match said expected test result; and a result processor for initiating generation of an alert message to a user indicating said first failure condition.

2. A system according to claim 1, wherein said
interface processor further receives user entered data identifying at least one further laboratory test result of said patient and user entered data identifying at least one further expected laboratory test result of said at least one further laboratory test; and
wherein said validation processor compares said at least one further laboratory test result with said at least one further expected laboratory test result and identifies a second failure condition in response to said at least one further laboratory test result of said patient failing to match said at least one further expected laboratory test result; and
wherein said result processor initiates generation of an alert message to a user indicating said second failure condition.

3. A system according to claim 1, wherein
said interface processor further receives user entered data identifying a plurality of validation pre-conditions for validating said laboratory test of said patient;
wherein said validation processor identifies a second failure condition when at least one of said plurality of validation pre-conditions are nor satisfied; and
wherein said result processor initiates generation of an alert message to a user indicating said second failure condition.

4. A system according to claim 3, wherein
one of said plurality of validation preconditions corresponds to an elapsed time period to wait before comparing said laboratory test result with said expected test result, said elapsed time period being a time period following initiation of said laboratory rest.

5. A system according to claim 1, wherein
said received user entered data identifying an expected result of said laboratory test comprises at least one of, (a) an identifier indicating a culture is resistant to a test compound, (b) an identifier indicating a culture is sensitive to a test compound, (c) an identifier indicating a positive test result and (d) an identifier indicating a negative test result.

6. A system according to claim 1, wherein
said received user entered data identifying an expected result of said laboratory test comprises a quantity identifier indicating presence of an approximate quantity of microbes per unit area of a culture.

7. A system according to claim 6, wherein
said quantity identifier identifies a qualitative range of said quantity of microbes per unit area, including at least one of (a) an identifier indicating "few" and (b) an identifier indicating "many".

8. A system according to claim 6, wherein
said microbes comprise at least one of, (a) a bacteria, (b) a fungi, (c) a parasite and (d) a virus.

9. A system according to claim 1, wherein
said received user entered data identifying an expected result of said laboratory test identifies at least one of, (a) a count value of number of microbes present per unit area of a culture, (b) a color of a microbe indicator, (c) a color change of a microbe indicator.

10. A system according to claim 1, wherein
said received user entered data identifies a plurality of expected results of said laboratory rest and said validation processor compares a plurality of laboratory test results with said plurality of expected results and identifies a failure condition in response to a predetermined condition if at least one of said plurality of laboratory test results fails to match a corresponding one of said plurality of expected results.

11. A system according to claim 1, wherein
said interface processor receives user entered data identifying a plurality of results expected for a corresponding plurality of test results derived at different time stages of a laboratory test,
said validation processor compares an individual result of said plurality of expected test results with a corresponding individual laboratory test result of said plurality of test results and identifies a failure condition in response to said individual laboratory test result failing to match said corresponding expected test result; and
said result processor initiates generation of an alert message to a user indicating a failure condition of said individual test performed at a particular time stage of said different rime stages.

12. A system according to claim 1, wherein
said result processor initiates generation of an alert message to a user in response to occurrence of said failure condition, said message at least one of, (a) prompting a user to initiate performance of another predetermined laboratory test, (b) informing a user of potential reasons for said failure condition, (c) prompting a user to repeat said laboratory test, (d) prompting a user with a user predetermined message and (e) identifying an expected result and actual result of said laboratory test.

13. A system according to claim 1, wherein
said result processor initiates generation of an alert message to a user prompting a user to enter an override command indicating whether said failure condition is to be overridden.

14. A system according to claim 13, wherein
said result processor initiates storage of a record indicating said failure condition was overridden, in response to said user override command,
said record at least one of, (a) being accessible by an authorized person, (b) providing an audit trail indicating a person entering said override command and (c) being incorporated in a report identifying override command occurrences.

15. A system according to claim 13, including
an authorization processor for determining whether a user is authorized to override said failure condition and to inhibit override in response to a determination said user is unauthorized.

16. A system according to claim 1, wherein
said result processor initiates generation of an alert message with a plurality of different warning severity message levels.

17. A user interface system for use processing information related to laboratory tests and results, comprising:
a display processor for initiating generation of at least one display image including display elements for,
enabling a user to enter data identifying a laboratory test result of a patient specimen culture and to enter data identifying an expected result of said laboratory test and one or more validation pre-conditions, and for
displaying an alert message to a user indicating a failure condition derived by employing one or more user determined validation pre-conditions in comparing said laboratory test result with said expected test result and by determining a failure condition in response to said laboratory test result failing to match said expected test result.

18. A user interface system according to claim 17, wherein said at least one display image includes display elements for enabling a user to enter data identifying an expected result of said laboratory test comprising at least one of (a) an identifier indicating a culture is resistant to a test compound, (b) an identifier indicating a culture is sensitive to a test compound, (c) an identifier indicating a positive test result and (d) an identifier indicating a negative test result and (e) a quantity identifier indicating presence of an approximate quantity of microbes per unit area of a culture.

19. A user interface system according to claim 17, wherein said at least one display image includes display elements for displaying an alert message to a user prompting a user to enter an override command indicating whether said failure condition is to he overridden.

20. A system for processing information related to laboratory tests and results, comprising:

an interface processor for receiving user entered data identifying a plurality of results expected for a corresponding plurality of test results derived at different time stages of a laboratory test;

a validation processor for employing one or more user determined validation pre-conditions in comparing an individual result of said plurality of expected test results with a corresponding individual laboratory test result of said plurality of test results and identifies a failure condition in response to said individual laboratory test result failing to match said corresponding expected test result; and a result processor for initiating generation of an alert message to a user indicating a failure condition of said individual test performed at a particular time stage of said different time stages.

21. A method for processing information related to laboratory tests and results, comprising the activities of:

receiving user entered data identifying a laboratory test result of a patient specimen culture;

receiving user entered data identifying an expected result of said laboratory test;

employing one or more user determined validation pre-conditions in comparing said laboratory test result with said expected test result;

identifying a failure condition in response to said laboratory test result failing to match said expected test result; and initiating generation of an alert message to a user indicating said failure condition.

22. A method for processing information related to laboratory tests and results, comprising the activities of:

receiving user entered data identifying a plurality of results expected for a corresponding plurality of test results derived at different time stages of a laboratory test;

employing one or more user determined validation pre-conditions in comparing an individual result of said plurality of expected test results with a corresponding individual laboratory test result of said plurality of test results;

identifying a failure condition in response to said individual laboratory test result failing to match said corresponding expected test result; and initiating generation of an alert message to a user indicating a failure condition of said individual test performed at a particular time stage of said different time stages.

23. A user interface system for processing information related to laboratory tests and results, comprising:

a display processor for initiating generation of at least one display image including display elements for, enabling a user to enter data identifying an expected laboratory test result, a laboratory test result; at least one further expected laboratory test result, at least one further laboratory test result; and a plurality of validation pre-conditions for validating said first laboratory test, and for displaying an alert message to a user indicating a failure condition derived by, employing one or more user determined validation pre-conditions in comparing said expected laboratory test result with said laboratory test result and identifying a first failure condition in response to said laboratory test result failing to match said expected laboratory test result;

comparing said at least one further laboratory test result with said at least one further expected laboratory test result and identifying a second failure condition in response to said at least one further laboratory test result failing to match said at least one further expected laboratory test result; and determining that at least one of said plurality of validation pre-conditions are not satisfied.

24. A method for processing information related to laboratory tests and results, comprising:

a) receiving user entered data comprising:

an expected first laboratory test result of a first laboratory test requiring validation processing;

an actual first laboratory test result;

at least one further expected laboratory test result of at least one further laboratory test for validating said first laboratory test; and at least one further actual laboratory test result of said at least one further laboratory test; and a plurality of validation pre-conditions;

b) employing one or more user determined validation pre-conditions in comparing said expected first laboratory test result with said actual first laboratory test result and identifying a first failure condition in response to said expected first laboratory test result failing to match said actual first laboratory test result;

c) comparing said at least one further expected laboratory test result with said at least one further actual laboratory test result and identifying a second failure condition in response to said at least one further expected laboratory test result failing to match said at least one further actual laboratory test result; and d) identifying a third failure condition when said plurality of validation pre-conditions are not satisfied.

25. The method of claim 24, further comprising the steps of initiating generation of an alert message to a user responsive to said first, second or third failure conditions.

* * * * *